(12) United States Patent
Leung et al.

(10) Patent No.: US 7,348,419 B2
(45) Date of Patent: Mar. 25, 2008

(54) HUMANIZATION OF AN ANTI-CARCINOEMBRYONIC ANTIGEN ANTI-IDIOTYPE ANTIBODY AS A TUMOR VACCINE AND FOR TARGETING APPLICATIONS

(75) Inventors: Shui-on Leung, Madison, NJ (US); Michele J. Losman, South Orange, NJ (US); Hans Hansen, Mystic Island, NJ (US)

(73) Assignee: Immunomedics, Inc., Morris Plains, NJ (US)

(*) Notice: Subject to any disclaimer, the term of this patent is extended or adjusted under 35 U.S.C. 154(b) by 309 days.

(21) Appl. No.: 10/808,538

(22) Filed: Mar. 25, 2004

(65) Prior Publication Data

US 2005/0048053 A1 Mar. 3, 2005

Related U.S. Application Data

(62) Division of application No. 09/155,106, filed as application No. PCT/US97/04696 on Mar. 19, 1997, now Pat. No. 6,730,300.

(60) Provisional application No. 60/013,708, filed on Mar. 20, 1996.

(51) Int. Cl.
C07H 21/04 (2006.01)

(52) U.S. Cl. ............... 536/23.1; 435/320.1; 530/387.1; 424/130.1

(58) Field of Classification Search ............. 424/131.1, 424/130.1, 133.1, 141.1; 435/320.1, 334, 435/69.1; 530/388.22, 387.1; 536/23.53, 536/23.1
See application file for complete search history.

(56) References Cited

U.S. PATENT DOCUMENTS

| 4,624,846 | A | 11/1986 | Goldenberg et al. |
| 4,818,709 | A | 4/1989 | Primus et al. |
| 5,443,953 | A | 8/1995 | Hansen et al. |

FOREIGN PATENT DOCUMENTS

| WO | WO 91/11465 | 8/1991 |
| WO | WO 94/04702 | 3/1994 |
| WO | WO 96/01126 | 1/1996 |
| WO | WO 96/11013 | 4/1996 |

OTHER PUBLICATIONS

Rudikoff et al (Proc. Natl. Acad. Sci. USA 1982 vol. 79 p. 1979).*
Genes IV (Lewin et al, Oxford University Press, p. 810, 1990).*
Mountain e al., "Engineering Antibodies for Therapy", Biotechnology and Engineering Reviews, Intercept Ltd., Dec. 1992, p. 1-142, vol. 10.
Graziano et al., "Construction and Characterization of Humanized Anti-y-lg Receptor type I (FcyRI) Monoclonal Antibody", The Journal of Immunology, The American Association of Immunologists, pp. 4996-5002, Nov. 1995.
Leung et al., "Humanization of an Anti-carcinoembryonic Antigen Anti-idiotype Antibody as a Tumor Vaccine and for Targeting Applications", Proceedings of the American Association for Cancer Research Annual Meeting, vol. 37, Mar. 1996, Meeting Info.: 87th Annual Meeting of the American Association for Cancer Research, Washington, D.C., USA; Apr. 20-24, 1996.
Losman et al., "Generation and Monitoring of Cell Lines Producing Humanized Antibodies", Clinical Cancer Research, pp. 3101s-3105s, Oct. 1999, vol. 5.
Losman, et al., Int. J. Cancer, 56-580-584, 1994.
Primus, et al., Cancer Research, 43:686, 1983.
Jones et al., Nature, 332:323, 1988.
Riechmann et al., Nature, 332: 323-327, 1988.
Irvine et al., Cancer Immunology Immunotherapy, 36:281-292, 1993.
Pimm et al., Life Sciences, 56(17); 1401-1406, 1995.
Gaida et al., Intl. J. Cancer, 51:459-465, 1992.
Morrison et al., Hospital Practice, pp. 65-69, 72-74, 77-78, 80, Oct. 15, 1989.
Evan et al., Q J Med. 92-299-307, 1999.
Jain, Cancer and Metastasis Reviews, 9:253-266, 1990.
Seaver, Genetic Engineering News, 14(14):10 and 21, Aug. 1994.
Reiger et al., Glossary of Genetics and Cytogenetics, Classical and Molecular, 4th Ed., Springer-Verlay, Berlin, 1976.
Michele J. Losman et al., "Mimicry of a Carcinoembryonic Antigen Epitope by a Rat Monoclonal Anti-Idiotype Antibody", Int. J. Cancer, 1994, pp. 580-584, vol. 56.
Bhattacharya, Chatterjee M., et al., "Murine monoclonal anti-idiotype antibody as a potential network antigen for human carcinoembryonic antigen," J. Immunol, Oct. 15, 1990, 145(8):2758-65.
Chakraborty, M., et al., "Preclinical evaluation in nonhuman primates of an anti-idiotypic antibody that mimicks the carcinoembryonic antigen," J. Immunother Emphasis Tumor Immunol. Aug. 18, 1995 (2):95:103.
Durrant, L.G., et al., "An idiotypic replica of carcinoembryonic antigen inducing cellular and humoral responses directed against human colorectal tumours," Int. J. Cancer, Mar. 12, 1992 (5):811-6.

* cited by examiner

Primary Examiner—David J. Blanchard
Assistant Examiner—Parithosh K. Tungaturthi
(74) Attorney, Agent, or Firm—Faegre & Benson, LLP

(57) ABSTRACT

A humanized form of an anti-idiotype antibody to CEA, e.g., hWI2, has conserved immunoreactivity. The clinical benefits of anti-CEA antibodies are maximized by using the humanized anti-idiotype as a clearing agent for anti-CEA antibodies or antibody fragments. The humanized anti-idiotype also can be used as an immunogenic vaccine.

9 Claims, 9 Drawing Sheets

```
KOL:       ----V-----GV---------R----SS----I--T--XXXXX--W--V--I-RQAPGEGLEWVA
RATWI2VH:  QVQLQESGGDLVQPGRSLKLSCVASGFFSNYWMT
KOLWI2VH-1:----V-----GV---------R----SS-------NYWMT-----K----------
KOLWI2VH-2:----V-----GV---------R----SS-------NYWMT-----K----------

XXXXXXXXXXSITSTGGTYHAE
                                                                   SITSTGGTYHAE
                                                                   SITSTGGTYHAE
                                                                   SITSTGGTYHAE

KOL:       ----------N--F---D-------GV--F--A-Y-C-S-R-XXXXXXXXXX DDYGGQSTYVMDA WGQGSSVTVSS
RATWI2VH:  RFTISRDNSKSTLYLQMNSLRPEDTATY         DDYGGQSTYVMDA ----TP----
KOLWI2VH-1:SVKG-------N--F---D-------GV------------ ------------- ----TP----
KOLWI2VH-2:SVKG-------N--F---D-------GV------------ ------------- ----TP----
```

FIG.1

```
REI:        ---M----S--S--V-----                    XXXXXXX   - Y   ---T---A-K---  XXXXXXX
RATWI2VK:   DIQLTQSPASLPASLGDRVTITC RASQDIGNYLR W F QQKPGKSPRLLIY GATNLAA
REIWI2VKRS:  ---M----S--S--V-----  RASQDIGNYLR  - -   ---T---A-K---  GATNLAA
REIWI2VK:    ---M----S--S--V-----  RASQDIGNYLR  - -   ---T---A-K---  GATNLAA

REI:        -----------G---T--Y TF--SS--QP--I-T---                XXXXXXXX  ---Q-----QI T -T
RATWI2VK:   GVPSRFSGS R SG S D F SLTINSLESEDMAIYYC LHHSEYPYT FG I GTKLER K R
REIWI2VKRS: -----------  - -  -  TF---SS--QP--I-T-  LHHSEYPYT   ---  ---QI T -
REIWI2VK:   -----------G---T---  TF---SS--QP--I-T-  LHHSEYPYT   ---  ---QI - -
```

```
oligo 21  caggtccaactgcaggagtcaggggaggtgtagtgcagcctggaa
                       [PstI]
          CAGGTCCAACTGCAGGAGTCAGGGGAGGTGTAGTGCAGCCTGGAAGGTCTCTGAGACTT
     1    ---------+---------+---------+---------+---------+---------+   60
          GTCCAGGTTGACGTCCTCAGTCCCCTCCACATCACGTCGGACCTTCCAGAGACTCTGAA    [oligo
                                                                         K]
          Q  V  Q  L  Q  E  S  G  G  G  V  V  Q  P  G  R  S  L  R  L  -
                      ↑
                  (Q to V mutation needed)

TCCTGTGCTCAGCTCCATCTGGATTCACATTCAGTAATTACTGGATGACTTGGATACGCCAGGCT
    61    ---------+---------+---------+---------+---------+---------+  120
[oligo K] AGGACATCGAGTAGACCTAAGTGTAAGTCATTAATGACCTACTGAACTATGCGGTCCGA
          S  C  S  S  S  G  F  T  F  S  N  Y  W  M  T  W  I  R  Q  A  -
                                            [KpnI]
          CCAGGGGAAGGGTCTTGAATGGGTTGCGTCCATTACTAGTACTGGTGGTGTACCTACCAT
   121    ---------+---------+---------+---------+---------+---------+  180
[oligo K] GGTCCCCTTCCCAGAACTTACCCAACGCAGGTAATGATCATGACCACCACCATGGATGTA
                                                   ccaacgcaggtaatgatcatgaccaccaccatggatggta
          P  G  K  G  L  E  W  V  A  S  I  T  S  T  G  G  G  T  Y  H  -
```

FIG. 3B

```
oligo
 23    atgcagagtctgtgaagggccgattcactatctccagagataattcaa
       GCAGAGTCTGTGAAGGGCCGATTCACTATCTCCAGAGATAATTCAAAAAACACCCTGTTC
 181   ---------+---------+---------+---------+---------+---------+ 240
       CGTCTCAGACACTTCCCGGCTAAGTGATAGAGGTCTCTATTAAGTTTTTTGTGGGACAAG  [oligo
                  cgtctcagacactt (oligo 22)                          L]
        A  E  S  V  K  G  R  F  T  I  S  R  D  N  S  K  N  T  L  F  -

CTGCAAATGGACAGTCTGAGGCCTGAGGACACGGGGGTTTATTACTGTGTTCAAGAGATGAC
 241   ---------+---------+---------+---------+---------+---------+ 300
       GACGTTTACCTGTCAGACTCCGGACTCCTGTGCCCCGCAAATAATGACAAGTTCTCTACTG
[oligo L]GACGTTTACCTGTCAGACTCCGGACTCCTGTGCCCCGCAAATAATGACAAGTTCTCTACTG
        L  Q  M  D  S  L  R  P  E  D  T  G  V  Y  Y  C  S  R  D  D  -
                                                          (BstEII)

TACGGAGGACAGAGACCACTTATGTTATGGATGCCTGGGGTCAGGGAACTCCGGTCACCGTC
 301   ---------+---------+---------+---------+---------+---------+ 360
       ATGCCTCCTGTCTCTGTGGATACAATACCTACGGACCCCAGTCCCTTGAGGCCAGTGGCAG
[oligo L]ATGCCTCCTGTCTCTGTGGATACAATACCTACGGACCCCAGTCCCTTGAGGCCAGTGGCAG
                                         caatacctacggacccccagtccccttgaggccagtggcag
        Y  G  G  Q  S  T  Y  V  M  D  A  W  G  Q  G  T  P  V  T  V  -

TCCTCC
 361   ------ 366
       AGGAGG
       aggagg (oligo 24)
        S  S  -
```

FIG. 4A

```
oligo 25 (PvuII)
        gacattcagctgaccagtctccatctccctgtctgctctgtgggaga
oligo 25 atgaccagtctccatctccctgtctgctctgtgggaga
        GACATTCAGATGACCCAGTCTCCATCTCCCTGTCTGCCTGTCTGTGGGAGACAGAGTCACT
      1 ---------+---------+---------+---------+---------+---------+ 60
        CTGTAAGTCTACTGGGTCAGAGGTAGAAGGACAGACGGCAGACACCCTCTGTCTCAGTGA  (oligo M)

D  I  Q  M  T  Q  S  P  S  S  L  S  A  S  V  G  D  R  V  T  -

ATTACTTGCCGGGCAAGTCAGAGACATTGGAAATTATTTAAGATGGTTCCAGCAGACACCG
     61 ---------+---------+---------+---------+---------+---------+ 120
        [oligo M]TAATGAACGGCCCGTTCAGTCTCTGTAACCTTTAATAAATTCTACCAAGGTCGTCTGTGGC

I  T  C  R  A  S  Q  D  I  G  N  Y  L  R  W  F  Q  Q  T  P  - oligo 27 tggctgcaggggtccatca
                                                                   [PstI]
          GGGAAAGCTCCGAGGCTTTGAAACTTTGATTTATGGTGCAACCAACTTGGCTGCAGGGGTCCCATCA
    121 ---------+---------+---------+---------+---------+---------+ 180
        [oligo M]CCCTTTCGAGGCTCCGAAACTTTGAAACTAAATACCACGTTGGTTGAACCGACGTCCCCAGGTAGT
                                                          actaaatataccacgttgaaccgacgtcccagg (oligo 26)

```
              cggttcagtggcagtgggtctggg
              CGGTTCAGTGGCAGTGGGTCTGGGACAGATTTTACTTTTACCATCTCAAGCCTTCAGCCT
      181     ----+----+----+----+----+----+----+----+----+----+----+----+    240
[oligo N]     GCCAAGTCACCGTCACCCAGACCCTGTCTAAAATGAAAATGGTAGAGTTCGGAAGTCGGA

R  F  S  G  S  G  T  D  F  F  T  I  S  S  L  Q  P   -

GAAGATATATTGCTACTTATTACTGTCTGCACCATTCTGAGTATCCATACACGTTTGGAATT
      241     ----+----+----+----+----+----+----+----+----+----+----+----+    300
[oligo N]     CTTCTATATAACGATGAATAATGACAGACGTGGTAAGACTCATAGGTATGTGCAAACCTTAA

E  D  I  A  T  Y  Y  C  L  H  H  S  E  Y  P  Y  T  F  G  I  -

GGGACCAAGTTGCAGATCAAACGTG                                  tgtgcaaaccttaa
      301     ----+----+----+-----    325
[oligo N]     CCCTGGTCAACGTCTAGTTTGCAC
                                    cctggttcaacgtctagattgcac (oligo 28)

G  T  K  L  Q  I  K  R   -
```

```
GACATTCAGC  TGACCCAGTC  TCCAGCTTCC  CTGCCTGCGT  CTCTGGGAGA      50
CTGTAAGTCG  ACTGGGTCAG  AGGTCGAAGG  GACGGACGCA  GAGACCCTCT
 D  I  Q  L   T  Q  S   P  A  S    L  P  A  S    L  G  D

CAGAGTCACT  ATTACTTGCC  GGGCAAGTCA  AGACATTGGA  AATTATTTAA      100
GTCTCAGTGA  TAATGAACGG  CCCGTTCAGT  TCTGTAACCT  TTAATAAATT
 R  V  T    I  T  C   R  A  S  Q   D  I  G    N  Y  L  R
                         ─────────  ─────────  ──────────
                                    CDR1

GATGGTTCCA  GCAGAAACCG  GGGAAATCTC  CGAGGCTTTT  GATTTATGGT      150
CTACCAAGGT  CGTCTTTGGC  CCCTTTAGAG  GCTCCGAAAA  CTAAATACCA
 W  F  Q    Q  K  P    G  K  S  P   R  L  L    I  Y  G
                                                        ─

GCAACCAACT  TGGCAGCTGG  GGTCCCATCA  CGGTTCAGTC  GCAGTAGGTC      200
CGTTGGTTGA  ACCGTCGACC  CCAGGGTAGT  GCCAAGTCAC  CGTCATCCAG
 A  T  N  L    A  A   G  V  P  S   R  F  S  G   S  R  S
─────────  ─────────  ──
    CDR2

TGGGTCAGAT  TTTTCTCTGA  CCATCAACAG  CCTGGAGTCT  GAAGATATGG      250
ACCCAGTCTA  AAAAGAGACT  GGTAGTTGTC  GGACCTCAGA  CTTCTATACC
 G  S  D    F  S  L  T   I  N  S    L  E  S    E  D  M  A

CTATTTATTA  CTGTCTGCAC  CATTCTGAGT  ATCCATACAC  GTTTGGAATT      300
GATAAATAAT  GACAGACGTG  GTAAGACTCA  TAGGTATGTC  CAAACCTTAA
 I  Y  Y   C  L  H   H  S  E  Y   P  Y  T    F  G  I
            ─────────  ─────────  ─────────  ──
                        CDR3

GGGACCAAGC  TGGAACGGAA  ACGG                                    324
CCCTGGTTCG  ACCTTGCCTT  TGCC
 G  T  K  L    E  R  K   R
```

FIG.6

```
CAGGTCCAAC  TGCAGGAGTC  AGGGGGAGAT  CTAGTGCAGC  CTGGAAGGTC        50
GTCCAGGTTG  ACGTCCTCAG  TCCCCCTCTA  GATCACGTCG  GACCTTCCAG
 Q  V  Q  L    Q  E  S    G  G  D    L  V  Q  P    G  R  S

TCTGAAACTT  TCCTGTGTAG  CCTCTGGATT  CACATTCAGT  AATTACTGGA       100
AGACTTTGAA  AGGACACATC  GGAGACCTAA  GTGTAAGTCA  TTAATGACCT
 L  K  L    S  C  V  A    S  G  F    T  F  S    N  Y  W  M
                                                 ─────────
                                                    CDR1
TGACTTGGAT  CCGCCAGGCT  CCAGGGGAGG  GTCTTGAATG  GGTTGCGTCC       150
ACTGAACCTA  GGCGGTCCGA  GGTCCCCTCC  CAGAACTTAC  CCAACGCAGG
 T  W  I    R  Q  A    P  G  E  G    L  E  W    V  A  S
 ─                                                     ─

ATTACTAGTA  CTGGTGGTGG  GACTTACCAT  GCAGAGTCTG  TGAAGGGCCG       200
TAATGATCAT  GACCACCACC  CTGAATGGTA  CGTCTCAGAC  ACTTCCCGGC
 I  T  S    T  G  G    T  Y  H    A  E  S  V    K  G  R
 ──────────────────────────────
              CDR2
ATTCACTATC  TCCAGAGATA  ATTCAAAAAG  CACCCTGTAC  CTGCAAATGA       250
TAAGTGATAG  AGGTCTCTAT  TAAGTTTTTC  GTGGGACATG  GACGTTTACT
 F  T  I    S  R  D  N    S  K  S    T  L  Y    L  Q  M  N

ACAGTCTGAG  GCCTGAGGAC  ACGGCCACTT  ATTACTGTTC  AAGAGATGAC       300
TGTCAGACTC  CGGACTCCTG  TGCCGGTGAA  TAATGACAAG  TTCTCTACTG
 S  L  R    P  E  D    T  A  T  Y    Y  C  S    R  D  D
                                                    ─  ─
TACGGAGGAC  AGAGCACCTA  TGTTATGGAT  GCCTGGGGTC  AGGGATCTTC       350
ATGCCTCCTG  TCTCGTGGAT  ACAATACCTA  CGGACCCCAG  TCCCTAGAAG
 Y  G  G  Q    S  T  Y    V  M  D    A  W  G  Q    G  S  S
 ──────────────────────────────────
              CDR3
GGTCACCGTC  TCCTCA                                               366
CCAGTGGCAG  AGGAGT
 V  T  V    S  S
```

Fig. 7 ly, and radiolabeled MN-14-Fab' can detect lesions as

HUMANIZATION OF AN ANTI-CARCINOEMBRYONIC ANTIGEN ANTI-IDIOTYPE ANTIBODY AS A TUMOR VACCINE AND FOR TARGETING APPLICATIONS

This application is a divisional of U.S. patent application Ser. No. 09/155,106, filed Nov. 17, 1998, now U.S. Pat. No. 6,730,300 which is a 371 of PCT/US97/04696, filed Mar. 19, 1997, which claims benefit of U.S. Provisional Application Ser. No. 60/013,708, filed Mar. 20, 1996. The entire contents of the above-identified application are hereby incorporated by reference.

BACKGROUND OF THE INVENTION

The present invention relates to chimeric and humanized anti-idiotype antibodies that specifically bind carcinoembryonic antigen antibodies. The invention further relates to the uses of the chimeric and humanized anti-idiotype antibodies as clearing agents in therapeutic methods, as a vaccine, and to detect in biological fluid samples the presence of an antibody or fragment thereof that specifically binds CEA.

The use of targeting monoclonal antibodies conjugated to radionuclides or other cytotoxic agents offers the possibility of delivering such agents directly to the tumor site, thereby limiting the exposure of normal tissues to toxic agents. (Goldenberg, *Semin. Nucl. Med.*, 19: 332 (1989)). In recent years, the potential of antibody-based therapy and its accuracy in the localization of tumor-associated antigens have been demonstrated both in the laboratory and clinical studies (see., e.g., Thorpe, *TIBTECH*, 11: 42 (1993); Goldenberg, *Scientific American, Science & Medicine*, 1: 64 (1994); Baldwin et al., U.S. Pat. Nos. 4,925,922 and 4,916,213; Young, U.S. Pat. No. 4,918,163; U.S. Pat. No. 5,204,095; Irie et al., U.S. Pat. No. 5,196,337; Hellstrom et al., U.S. Pat. Nos. 5,134,075 and 5,171,665). In general, the use of radiolabeled antibodies or antibody fragments against tumor-associated markers for localization of tumors has been more successful than for therapy, in part because antibody uptake by the tumor is generally low, ranging from only 0.01% to 0.001% of the total dose injected (Vaughan et al., *Brit. J. Radiol.*, 60: 567 (1987)). Increasing the concentration of the radiolabel to increase the dosage to the tumor is counterproductive generally as this also increases exposure of healthy tissue to radioactivity.

Carcinoembryonic antigen (CEA) is a 180,000-Da glycoprotein expressed in most adenocarcinomas of endodermal-derived digestive-system epithelia and in some other types of cancer such as breast cancer and non-small-cell lung cancer. One of the main advantages of the CEA system is that AB1 anti-CEA have been extensively used as radioimmunodetection agents in cancer patients. One such antibody, MN-14, is a murine $IgG_1K$ monoclonal antibody (Mab) with high affinity ($K_D=10^{-9}M$) for human CEA. In cancer patients, $^{131}I$-MN-14 targets CEA-producing tumors effectively, and radiolabeled MN-14-Fab' can detect lesions as small as 2 cm in diameter.

Rat anti-idiotype antibody (rWI2) against an anti-carcinoembryonic antigen antibody (MN-14) has been considered as a potential idiotype vaccine, capable of eliciting an Ab3 response in immunized animals. Losman et al., *Int. J. Cancer* 56: 580-584 (1994). It has also been shown that WI2 can serve as an effective clearing agent improving tumor/nontumor ratios and reducing myelotoxicity, when used to remove excess radiolabeled MN-14, as shown, for example, in U.S. Pat. No. 4,624,846, the entire contents of which are incorporated herein by reference. However, its use is limited by the short biological half life of the rat Ab, due to rejection by the human host.

SUMMARY OF THE INVENTION

It is an object of the present invention to provide a chimeric anti-idiotype Ab with anti carcinoembryonic-antibody properties, a humanized anti-idiotype Ab with anti carcinoembryonic-antibody properties as an immunological reagent useful in clearing an organism of anti-CEA antibody initially used as a cancer treatment, diagnostic, or vaccine, where the anti-idiotype Ab has the immunogenic properties of a human MAb in a human patient, and to provide an anti-idiotype Ab with anti carcinoembryonic-antibody properties which can serve as a detection agent or vaccine. It is another object of the present invention to provide DNA constructs encoding such antibodies.

To achieve these objectives, in one aspect of the invention, a chimeric anti-idiotype antibody or fragment thereof which specifically binds to the idiotype region of an anti-CEA monoclonal antibody is provided, comprising the rWI2 light chain and heavy chain variable regions, or silent mutations thereof. In a preferred embodiment, the heavy chain variable region comprises the rWI2VH sequence shown in FIG. 1 (SEQ ID NO:18) and the light chain variable region comprises the rWI2VK sequence shown in FIG. 2 (SEQ ID NO:22).

In another aspect of the invention, a humanized anti-idiotype antibody or fragment thereof which specifically binds the idiotype region of an anti-CEA monoclonal antibody is provided, comprising rWI2 CDR regions and humanized FR regions. In a preferred embodiment, the heavy chain variable region comprises the KOLWI2VH-1 (SEQ ID NO:19) or the KOLWI2VH-2 (SEQ ID NO:20) sequence shown in FIG. 1 and the light chain variable region comprises the REIWI2VK (SEQ ID NO:24) or the REIWI2VKRS (SEQ ID NO:23) sequence shown in FIG. 2.

In another aspect of the invention, an isolated polynucleotide encoding the heavy chain or the heavy chain variable region of a chimeric or humanized antibody or antibody fragment which specifically binds the idiotype region of an anti-CEA monoclonal antibody is provided, comprising sequences enclosing at least two rWI2 heavy chain CDRs, selected from the group of CDRs consisting of:

the complementary determining region-1 (CDR-1) sequence NYWMT(SEO ID NO:1), the complementary determining region-2 (CDR-2) sequence SITSTGGGTYHAESVKG (SEQ ID NO:2), and the complementary determining region-3 (CDR-3) sequence DDYGGQSTYVMDA (SEQ ID NO:3).

In another aspect of the invention, an isolated polynucleotide encoding the light chain or the light chain variable region of a chimeric or humanized antibody or antibody fragment which specifically binds the idiotype region of an anti-CEA monoclonal antibody is provided, comprising sequences enclosing at least two rWI2 CDRS, selected from the group of CDRs consisting of:

the complementary determining region-1 (CDR1) sequence RASQDIGNYLR (SEQ ID NO:4), the complementary determining region-2 (CDR2) sequence GATNLAA (SEQ ID NO:5), and the complementary determining region-3 (CDR3) sequence LHHSEYPYT (SEQ ID NO:6).

In another aspect of the invention, an isolated first expression vector comprising a gene for the chimeric WI2 heavy chain and an isolated second expression vector comprising a gene for the chimeric WI2 light chain are provided.

In another aspect of the invention, an isolated first expression vector comprising a gene for a humanized WI2 heavy chain and an isolated second expression vector comprising a gene for a humanized WI2 light chain are provided.

In another aspect of the invention, a host is provided, comprising an isolated first vector comprising a gene for the chimeric WI2 heavy chain and an isolated second expression vector comprising a gene for the chimeric WI2 light chain, or an isolated first expression vector comprising a gene for a humanized WI2 heavy chain and an isolated second expression vector comprising a gene for a humanized WI2 light chain.

In another aspect of the invention, a method of stimulating an immune response in a patient against cancers expressing carcinoembryonic antigen is provided, which comprises administering to a patient an effective amount of a vaccine comprising a humanized anti-idiotype antibody or fragment which specifically binds the idiotype region of an anti-CEA monoclonal antibody, conjugated to a soluble immunogenic carrier protein, optionally in combination with a pharmaceutically acceptable vaccine adjuvant.

In another aspect of the invention, a method of diagnosis or treatment of a patient is provided, wherein an antibody or antibody fragment that specifically binds CEA is used as a targeting, pre-targeting or therapy agent, either as such or as a component of a conjugate, the improvement to the method consisting of an anti-idiotype antibody used to clear non-targeted antibody or antibody fragment.

In another aspect of the invention, a method of detecting the presence of an antibody or fragment that specifically binds CEA, in a fluid biological sample, comprising contacting the sample with rWI2, or a chimeric anti-idiotype antibody or antibody fragment which specifically binds the idiotype region of an anti-CEA monoclonal antibody, or a humanized anti-idiotype antibody or antibody fragment which specifically binds the idiotype region of an anti-CEA monoclonal antibody, and detecting binding of said anti-idiotype antibody or antibody fragment to an antibody idiotype or antibody idiotype fragment in said sample.

DESCRIPTION OF THE FIGURES

FIG. 1 shows the design of the hVH. The rVH is shown aligned with KOL, and with the designed KOLWI2VH-1 (SEQ ID NO:19) and 2 (SEQ ID NO:20) sequences. Dashes indicate that the sequence matches at that position in the rWI2VH sequence (SEQ ID NO:18). Narrow boxes indicate positions where the rat aa was retained in the humanized FR sequences. Note that the KOLWI2VH-1 (SEQ ID NO:19) sequence contains an extra rat aa, when compared with KOLWI2VH-2 (SEQ ID NO:20), at position 5. CDRs are indicated by wider boxes.

FIG. 2 shows the design of hVK. The rWI2VK (SEQ ID NO:22) sequence is shown aligned with REI, and with the designed REIWI2VK (SEQ ID NO:24) and REIWI2VKRS (SEQ ID NO:23). Dashes indicate that the sequence matches at that position in the rWI2VK (SEQ ID NO:22) sequence. Narrow boxes indicate positions where the rat aa was retained in the humanized FR sequences. As indicated, four rat aa residues where retained in the FR regions. CDRs are indicated by wider boxes.

FIG. 3A-3B shows the polynucleotide sequence for the hWI2 heavy chain variable region (SEQ ID NO:25). The PCR primers employed and the synthesized oligo K and oligo L described in the text are indicated. A single aa letter code is given below the polynucleotide sequence to represent the translation product. The CDRs (SEQ ID NOs:1, 2 and 3) are underlined on the protein sequence.

FIG. 4A-4B shows the polynucleotide sequence for the hWI2 light chain variable region (SEQ ID NO:27). The PCR primers employed and the synthesized oligo M and oligo N described in the text are indicated. A single aa letter code is given below the polynucleotide sequence for the translation product. The CDRs (SEQ ID NOs:4, 5 and 6) are underlined on the protein sequence.

FIG. 6 shows the nucleic acid sequence for the variable region of rWI2 light chain (SEQ ID NO:29). The protein translation product is indicated below the nucleic acid sequence, using one letter aa code (SEQ ID NO:29). The aa residues representing CDRs 1-3 (SEQ ID NOs:4, 5 and 6) are underlined and labeled.

FIG. 7 shows the nucleic acid sequence for the variable region of rWI2 heavy chain (SEQ ID NO:31). The protein translation product is indicated below the nucleic acid sequence, using one letter aa code (SEQ ID NO:31). The aa residues representing CDRs 1-3 (SEQ ID NOs:1, 2 and 3) are underlined and labeled.

ILLUSTRATIVE GLOSSARY

Figure 5:
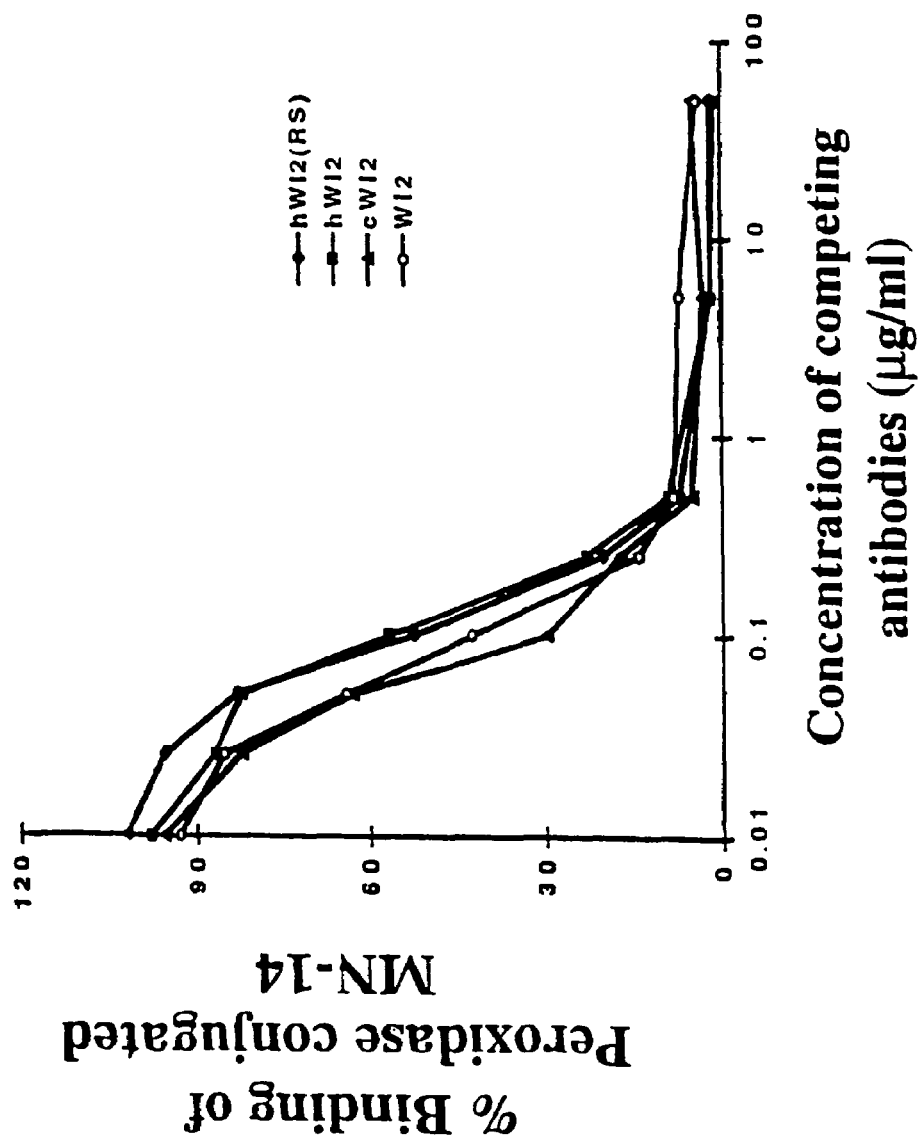
FIG. 5 shows a comparison between hWI2(RS), hWI2, cWI2, and rWI2 in competitive binding assays. Binding of each of these antibodies is shown as a percentage of inhibition of the binding by a peroxidase conjugated MN-14 antibody.

The following terms or abbreviations are used in the present application. The meanings set out in this glossary are for illustrative purposes only. The full meaning of the terms will be apparent to those of skill in the art.

"CDR" is used as an abbreviation for Complementarity Determining Region. These are the regions within the variable regions of an antibody that are primarily, but not exclusively, responsible for antigen-antibody binding.

"FR" is an abbreviation for Framework Region. Broadly speaking, these are the portions of the variable regions of an antibody which lie adjacent to or flank the CDRs. In general, these regions have more of a structural function that affects the conformation of the variable region and are less directly responsible for the specific binding of antigen to antibody, although, nonetheless, the framework regions can affect the interaction.

An "antibody-binding region" is that part of an antibody that overall is responsible for maintaining the structure of the antibody that interacts with the antigen. Generally, that is the combined light and heavy variable domains of an antibody.

As used herein, "Chimeric" refers to an antibody in which the variable region is derived from a rat antibody and the constant region is derived from a human antibody.

"Humanized" refers to a chimeric antibody as defined above, but in which the FR variable regions are modified to make them more similar in sequence to a human antibody.

A promoter is a DNA sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter.

An isolated DNA molecule is a fragment of DNA that is not integrated in the genomic DNA of an organism. For example, a cloned T cell receptor gene is a DNA fragment that has been separated from the genomic DNA of a mammalian cell. Another example of an isolated DNA molecule is a chemically-synthesized DNA molecule that is not integrated in the genomic DNA of an organism.

Complementary DNA (cDNA) is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

The term expression refers to the biosynthesis of a gene product. For example, in the case of a structural gene, expression involves transcription of the structural gene into mRNA and the translation of mRNA into one or more polypeptides.

A cloning vector is a DNA molecule, such as a plasmid, cosmid, or bacteriophage, that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

An expression vector is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

A recombinant host may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

As used herein, a silent mutation is a change introduced to the coding sequence of an antibody gene, which results in the expression of an antibody altered in its aa sequence, but, which is otherwise substantially similar to the antibody whose sequence was not altered, in respect to immune activity.

A tumor associated antigen is a protein normally not expressed, or expressed at very low levels, by a normal counterpart. Examples of tumor associated antigens include α-fetoprotein and carcinoembryonic antigen (CEA).

In the present context, an anti-CEA MAb is a Class III MAb, as described by Primus et al., *Cancer Research* 43: 686 (1983) and by Primus et al., U.S. Pat. No. 4,818,709, which are incorporated by reference.

As used herein, an Ab1 is an antibody that binds with a tumor associated antigen.

An anti-idiotype antibody (Ab2), as used herein, is an antibody that binds with an Ab1. Importantly, an Ab2 binds with the variable region of Ab1 and thus, an Ab2 mimics an epitope of a tumor associated antigen or an epitope of an infectious agent associated antigen.

An antibody fragment is a portion of an antibody such as $F(ab')_2$, $F(ab)_2$, Fab', Fab, and the like. Regardless of structure, an antibody fragment binds with the same antigen that is recognized by the intact antibody. For example, an anti-CEA Mab (Ab1) fragment binds with CEA, while an Ab2 fragment binds with the variable region of the Ab1 and mimics an epitope of CEA.

The term "antibody fragment" also includes any synthetic or genetically engineered protein that acts like an antibody by binding to a specific antigen to form a complex. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker ("sFv proteins"), and minimal recognition units consisting of the amino acid residues that mimic the hypervariable region.

As used herein, the term antibody component or the term antibody may include both an entire antibody and an antibody fragment.

Vaccine as used in the present context is an antibody or antibody fragment which is engineered to more effectively stimulate an immune response. Typically, this is achieved by conjugation of the antibody component to a soluble immunogenic carrier protein.

DETAILED DESCRIPTION OF THE INVENTION

An overview. Providing chimeric and humanized WI2 anti-idiotype antibodies.

Rat WI2 (rWI2) is an anti-idiotype monoclonal antibody which binds the CDR of MN-14. See Losman et al., (1994) supra. It was previously proposed that PCR primer pairs may be designed which might isolate the variable regions of rat antibodies from a RNA substrate. See Kutemeier et al., *Hybridoma*, 11: 23-32 (1992). Similar approaches have been employed to isolate the variable regions of mouse antibodies. See Orlandi et al., *Proc. Nat'l Acad. Sci.* USA 86: 3833 (1989). In the present invention, a combination of PCR primers as described by Kutemeier et. al., and by Orlandi et al., supra, are required to isolate the rWI2 variable region. These primers could be used to isolate other rat variable regions.

cDNA for the variable regions of both the light and heavy chains of rWI2 are isolated and the sequence from a number of clones is confirmed. The rat variable regions are cloned into plasmid vectors, such that the rat variable K and H regions are attached to respective human IgG constant regions. The plasmids are transfected into SP2/O cells, clones comprising both plasmids are selected, and chimeric WI2 (cWI2) antibody is expressed.

To humanize the variable regions, FR rat regions are replaced by the human IgG counterparts. The rat CDR regions are preserved, in order to maintain the specificity of the antibody. However, to enhance stability and maintain specificity and binding affinity of the antibody, it is best to employ a human sequence which is most similar to the newly identified rat FR sequences. Rat residues that are close to the CDRs, or known from prior experience to be important for interactions with the CDRs, were retained in both humanized sequences.

For both the heavy and light chain, long oligonucleotides corresponding to the variable region are engineered to reflect the humanized design. The oligonucleotides replace the rat variable region in plasmid constructs designated to produce full length human WI2 (hWI2). The effectiveness of cWI2 or hWI2 are compared with that of rWI2 in assays where they compete with CEA for binding to a peroxidase conjugated MN-14.

In order to express the cWI2 and the hWI2s, the rat and the humanized variable regions are inserted into one or separate plasmid vectors in such a manner as to allow coexpression of full length light and heavy antibody chains. The vectors can be transfected into SP2/O cells. Selection of transfected cells, and eventual amplification of the clones, are based on the expression of the dihydrofolate reductase (DHFR) gene which is located on the same plasmid vector. The functionality of various constructs is determined by binding assays. For example, final hWI2 constructs were compared with both rWI2 and cWI2 in their ability to bind MN-14—see FIG. 5.

Production of Monoclonal Ab1 and Ab2 Antibodies

Rodent monoclonal antibodies to specific antigens may be obtained by methods known to those skilled in the art. See, for example, Kohler and Milstein, *Nature* 256: 495 (1975), and Coligan et al. (eds.), CURRENT PROTOCOLS IN IMMUNOLOGY, VOL. 1, pages 2.5.1-2.6.7 (John Wiley & Sons 1991) [hereinafter "Coligan"]. Briefly, monoclonal antibodies can be obtained by injecting rats with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures. These techniques are applicable for production of a monoclonal antibody from other mammals injected with an antigen.

A wide variety of monoclonal antibodies against tumor associated antigens or infectious agents have been developed. See, for example, Goldenberg et al., international application publication No. WO 91/11465 (1991), and Goldenberg, international application publication No. WO 94/04702 (1994), each of which is incorporated herein by reference in its entirety.

Polyclonal Ab2 can be prepared by immunizing animals with Ab1 or fragments, using standard techniques. See, for example, Green et al., "Production of Polyclonal Antisera," in METHODS IN MOLECULAR BIOLOGY: IMMUNOCHEMICAL PROTOCOLS, Manson (ed.), pages 1-12 (Humana Press 1992). Also, see Coligan at pages 2.4.1-2.4.7. Alternatively, monoclonal Ab2 can be prepared using Ab1 or fragments as immunogen with the techniques described above.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

The Design of a Humanized Antibody

One antibody of the present invention is a "humanized" monoclonal antibody. That is, rat complementarity determining regions are transferred from heavy and light variable chains of the rat immunoglobulin into a variable region designed to contain a number of aa residues found within the FR region in human IgG. Similar conversion of mouse/human chimeric antibodies to a humanized antibody has been described before. General techniques for cloning murine immunoglobulin variable domains are described, for example, by the publication of Orlandi et al., *Proc. Nat'l Acad. Sci.* USA 86: 3833 (1989), which is incorporated by reference in its entirety. Techniques for producing humanized MAbs are described, for example, by Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci.* USA 89: 4285 (1992), Sandhu, *Crit. Rev. Biotech.* 12: 437 (1992), and Singer et al., *J. Immun.* 150: 2844 (1993), each of which is hereby incorporated by reference.

Construction of cWI2 and hWI2.

The engineering of chimeric and humanized WI2 employs standard molecular biology and cellular biology approaches, for example PCR reactions, sequencing of DNA, synthesis of long oligonucleotides, cloning, site-directed mutagenesis, transfection of vectors into cells, expression of chimeric and humanized antibodies, their purification and so on. The techniques employed are standard techniques, well known in the art and well established. A person skilled in the art would have no difficulty carrying out those techniques. All necessary materials are readily available. Reference manuals describing these techniques are widely available. For example, see Sambrook et al., *Molecular Cloning: A Laboratory Manual*, second ed., Cold Spring Harbor Press, (1989); Co et al., *J. Immunol.*, 148: 1149 (1992); Ausubel et al., eds., CURRENT PROTOCOLS IN MOLECULAR BIOLOGY, and updates, John Wiley & Sons, NY, (1987); "Protocols—Current Methods and Applications" White, ed., *Methods in Mol. Biol.* (15), Humana Press, Totawa, N.J. (1993); Uhlmann, *Gene* 71: 29 (1998); Wosnick et al., *Gene* 60: 115 (1988); and Huse, in ANTIBODY ENGINEERING: A PRACTICAL GUIDE, Boerrbaeck, ed., W.H. Freeman & Co., 103-120 (1992).

The PCR primers used in the initial cloning of the rat variable region are designed over regions of the sequence that are expected to be relatively conserved between human antibodies. Furthermore, an amino acid (aa) can generally be represented by more than one codon, although the codons often differ only in the third position. Such codons are sometimes referred to as "degenerate." To design the PCR primer one attempts to choose a protein sequence over which degenerate codons are limited in number. The approach is further limited by the need to design over a conserved protein sequence, as discussed above. Therefore, often, the "primer" as designed actually consists of a mix of numerous molecules that differ in sequence at specific positions. Any one primer molecule, which would provide a perfect match for the specific mRNA substrate to be amplified is present as a minuscule fraction of the overall primer mix. To enhance likelihood of success, a few primer pairs, i.e. covering different regions of the mRNA are generally tried.

One skilled in the art recognizes that alternative techniques are readily available. For example, initial changes to the cloned rat variable region could be introduced by any of a number of site specific mutagenesis protocols. Furthermore, it should be realized that additional aa changes in the variable and especially the FR regions may be possible, with the expectation that there will be some changes which would be silent in nature. Silent changes are those replacements, deletion or addition of one or a small number of aa that would not significantly affect the binding affinity or specificity of the antibody or antibody fragments thereof. Most obvious among such silent changes would be the replacement of one aa by an aa of a similar size and chemical properties. Such changes are well known in the art and are generally referred to as a "conservative" aa substitution. For example, a leucine when replaced by an isoleucine would generally not be expected to affect the structure of a protein. All such conserved aa changes, as well as silent changes which do not significantly affect the binding affinity or specificity of the anti-carcinoembryonic antibody, are within the scope of the invention.

Expression of the Engineered cWI2 or hWI2

Genes encoding the antibodies of the invention are introduced via expression vectors into a host cell, for expression. In a preferred embodiment, the genes for both the light and heavy genes are introduced in a single expression vector, which is introduced in a host cell. The expression vectors generally contain drug markers for selection of the transformed cell. A drug marker can furthermore be used to amplify the copy number of nearby genes, resulting in a clone overexpressing the antibody. For example, a vector expressing the light and heavy chains of cWI2 or hWI2 were introduced into SP2/O cells on vectors containing the DHFR gene. The original clones were amplified after selection by growth on methotrexate (MTX).

It should be understood that alternative ways to coexpress the light and heavy chain genes are feasible. A skilled artisan could consider other selection regimens, introduction of both the light and heavy chain genes on one plasmid or cotransformation with separate vectors encoding the light and heavy genes, and transfection of other cell lines. Furthermore, expression of the antibody in yet other systems is possible. For example, expression could occur in yeast. Alternatively, baculoviruses can be engineered with the light and heavy genes and expressed in cultured cells, or used to infect an insect.

The antibodies require purification from their expression system and media by methods that are generally similar to methods described above for purification of MAbs from hybridomas.

Uses for the Antibodies of the Invention

Humanized monoclonal antibodies in accordance with the invention are suitable for use in therapeutic methods. For example, MN-14 has been proposed as a therapeutic agent or as a vaccine to stimulate Ab2. The dosage of MN-14 conjugated to a drug can be enhanced if removal or clearing of unbound MN-14 is made possible by its binding, and aggregate formation, with hWI2. Similarly, MN-14 can be used as a vaccine, optionally by alternative applications with an anti-idiotype antibody vaccine. Delivery of the Ab2 would be counterproductive in the presence of excess, free-floating MN-14 vaccine. Here, hWI2, for example, would clear the MN-14 vaccine, to allow efficient administration of the Ab2 vaccine.

In addition, hWI2 itself can be a vaccine. Generally, the antibodies and fragments of the present invention can be used as vaccines by conjugating the antibodies or fragments to a soluble immunogenic carrier protein. Suitable carrier proteins include keyhole lympet hemocyanin, which is the preferred carrier protein. The antibodies and fragments can be conjugated to the carrier protein using standard methods. See, for example, Hancock et al, "Synthesis of Peptides for Use as Immunogen," in METHODS IN MOLECULAR BIOLOGY: IMMUNOCHEMICAL PROTOCOLS, Manson (ed.), pages 23-32 (Humana Press 1992).

A preferred vaccine composition comprises an antibody conjugate or fragment conjugate, and an adjuvant. Examples of suitable adjuvant include aluminum hydroxide and lipid. Methods of formulating vaccine compositions are well-known to those of ordinary skill in the art. See, for example, Rola, "Immunizing Agents and Diagnostic Skin Antigens," in REMINGTON'S PHARMACEUTICAL SCIENCES, 18th Edition, Gennaro (ed.), pages 1389-1404 (Mack Publishing Company 1990).

Additional pharmaceutical methods may be employed to control the duration of action of a vaccine in a therapeutic application. Controlled release preparations can be prepared through the use of polymers to complex or adsorb the antibodies or fragments. For example, bio-compatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release of an antibody or antibody fragment from such a matrix depends upon the molecular weight of the antibody or fragment, the amount of antibody or fragment within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990).

The anti-idiotype Ab of the invention can be used for the detection of an anti-carcinoembryonic antibody. For example, rWI2, cWI2 and hWI2 can be used in vitro to test the blood sample of a patient for the presence of anti-carcinoembryonic antibody. Detection of MN-14 levels, when MN-14 is used as a therapeutic agent or as a vaccine would be important. Presence of MN-14 can be detected by rWI2, cWI2, or hWI2. Similarly, hWI2 can be used in a patient to determine the presence of natural anti-CEA Abs. To be useful in the detection of an anti-CEA Ab, the anti-idiotype Abs can be conjugated to a label. Suitable labels include, e.g., a radiolabel, an enzyme, or a fluorescent label. Such labeling agents and methods of conjugation are well known to one skilled in the art.

The antibody preparations of the present invention can be formulated according to known methods to prepare pharmaceutically useful compositions, whereby antibodies or antibody fragments are combined in a mixture with a pharmaceutically acceptable carrier. A composition is said to be a "pharmaceutically acceptable carrier" if its administration can be tolerated by a recipient mammal. Sterile phosphate-buffered saline is one example of a pharmaceutically acceptable carrier. Other suitable carriers are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990).

The antibodies or fragments may be administered to a mammal intravenously or subcutaneously. Moreover, the administration may be by continuous infusion or by single or multiple boluses. Preferably, an antibody vaccine is administered subcutaneously, while an antibody preparation that is not a vaccine is administered intravenously. In general, the dosage of administered antibodies or fragments for humans will vary depending upon such factors as the patient's age, weight, height, sex, general medical condition and previous medical history. Typically, it is desirable to provide the recipient with a dosage of antibodies or fragments which is in the range of from about 1 pg/kg to 10 mg/kg (amount of agent/body weight of patient), although a lower or higher dosage also may be administered as circumstances dictate.

For purposes of therapy, antibodies or fragments are administered to a mammal in a therapeutically effective amount. An antibody preparation is said to be administered in a "therapeutically effective amount" if the amount administered is physiologically significant. An agent is physiologically significant if its presence results in a detectable change in the physiology of a recipient mammal. In particular, an antibody preparation of the present invention is physiologically significant if its presence invokes a humoral and/or cellular immune response in the recipient mammal.

The present invention, in addition to the specifically described techniques, cell lines, and vectors, relies on descriptions of said techniques, cell lines, and vectors presented in U.S. Pat. Nos. 5,443,953, and 4,624,846 and in U.S. patent application Ser. Nos. 08/318,157, and 08/289,576, all of which are incorporated herein by reference in their entireties.

EXAMPLE 1

Humanization of the WI2 Clone

The sequences encoding the WI2 VH and VK domains were obtained by reverse transcriptase followed by PCR reactions (RT-PCR) using RNA prepared from WI2 hybridomas as the templates. Since the WI2 antibody sequences were of rat origin, the Orlandi VH1FOR/BACK and VK1FOR/BACK primers sets might not be useful for their PCR-cloning. See Orlandi et al., 1989, supra. Based on the sequences suggested by Kutemeier et al., supra, primers were synthesized the following sets of primers for the PCR cloning of the VH and VK domains of WI2:

1BACK also produced a PCR product of the expected size, which was not further analyzed. FIG. 7 shows the sequence of the heavy chain variable region (SEQ ID NO:31).

The cloning of VK sequence

First-strand cDNA was prepared from total RNA isolated from WI2 hybridoma using random hexamers as the annealing primers. The RK1 (which anneals to rat CK domain) in conjunction with RVK-3BACK (which anneal to the 5' VK region), was used to PCR-amplify and isolate the VK region of rWI2, employing standard PCR protocols. The expected 320 base pairs (bp) product was obtained. The PCR product was further analyzed. Other primer pairs were not tested. FIG. 6 shows the sequence of the light chain variable region.

Restriction analysis of the 320 bp VK PCR product revealed the presence of an additional PvuII site which would interfere with subsequent cloning into the PvuII/BcII sites of the staging vector, VKpBR. Id. Because the PCR product lacked the appropriate ends for the staging vector, it was directly subcloned into the TA Cloning Vector (Invitrogen), which allowed for direct insertions of PCR DNA. Six individual clones were sequenced and all six were shown to be identical. Analysis of the deduced protein sequence indicated a functional VK domain. To subclone the sequence into a staging vector, a new primer was designed. In this primer, a PvuII compatible end, rather than the whole restriction recognition site, was introduced so that the PCR product would have on its 5' end a compatible site for ligation into the corresponding PvuII site within the VKPBR

```
(RCH1)      5'-GAC GTA TAC CTG TGG TTT TCT G-3',                      (SEQ ID NO:7)

(RVH-1BACK) 5'-AGG TSM ARC TGC AGS AGT CWG G-3', and                  (SEQ ID NO:8)

(RVH-1FOR)  5'-TGA GGA GAC GGT GAC CGT GGT CCC TTG GCC CC-3',         (SEQ ID NO:9)
            where S = G + C; M = A + C; R = A + G; and W = A + T, and (RK1)       5'-GGA TGA TGT CTT ATG AAC AA-3',                         (SEQ ID NO:10)

(RVK-1BACK) 5'-CCA GTT CCG AGC TCG TGC TCA CCC AGT CTC CA-3',         (SEQ ID NO:11)

(RVK-2BACK) 5'-CCA GTT CCG AGC TCC AGA TGA CCC AGT CTC CA-3',         (SEQ ID NO:12)

(RVK-3BACK) 5'-CCA GAT GTG AGC TCG TGA TGA CCC AGA CTC CA-3',         (SEQ ID NO:13)

(RVK-4BACK) 5'-CCA GAT GTG AGC TCG TCA TGA CCC AGT CTC CA-3',         (SEQ ID NO:14)

(RVK-5BACK) 5'-CCA GTT CCG AGC TCG TGA TGA CAC AGT CTC CA-3', and     (SEQ ID NO:15)

(RVK-1FOR)  5'-GTT AGA TCT CCA GCT TGG TCC C-3'.                      (SEQ ID NO:16)
```

The cloning of VH Sequence

First-strand cDNA was prepared from total RNA isolated from WI2 hybridoma using random hexamers as the annealing primers. RCH1 (which anneals to the rat IgG1 CH1 domain) and RVH-1BACK (which anneals to rat 5' VH region) were tried as a primer pair to PCR-amplify and isolate the VH sequence from the first-strand cDNA template, using standard protocols. However, no PCR product was obtained. Unexpectedly, the RCH1 primer, in conjunction with the Orlandi primer VH1BACK (5'-AGG TSM ARC TGC AGS AGT CWG G-3') (SEQ ID NO:8) produced a PCR product of the expected size. The PCR-amplified VH sequence was digested with the restriction enzymes PstI/BstEII and subcloned into the corresponding sites of the heavy chain staging vector, VHpBS. See Leung et at., Hybridoma 13: 469 (1994). Six individual clones were sequenced and confirmed to be identical to each other. RVH-1FOR which anneals to rat 3' VH region and RVH-staging vector. The PCR product was digested with BglII and subcloned into the PvuII/BcII cloning sites of the VKpBR staging vector. Id. The ligation was transformed in E. coli, and plated on selective plates. Miniprep DNA was prepared and analyzed. DNA from positive clones were sequenced to make sure that the joining region, at the PvuII site, was as expected. The PCR-amplified VH and VK sequence for WI2 were excised from their respective staging vector by HindIII/BamHI restriction digestion and the isolated fragments were subcloned into their respective heavy and light chain expression vectors, pG1g and pKh. Id. Chimeric WI2 (cWI2) was purified from clones cotransfected with the heavy and light chain expression vectors and the immunoreactivity of cWI2 was compared to that of rat WI2. Results indicated that both antibodies inhibited the binding of MN-14 onto CEA to a similar extent, confirming the functionality of the chimeric antibody, and the authenticity of the VH and VK sequences.

Design of the Humanized WI2 Sequence

VH and VK Design

By comparing the sequence homology of a number of human IgG to the rWI2 frame work region, the human KOL framework was chosen for grafting the heavy chain CDRs. Two versions of the humanized heavy chain designated as KOLWI2VH-1 and KOLWI2VH-2 were designed. See FIG. 1. However, only the KOLWI2VH-1 was synthesized and tested. KOLWI2VH-1 differs from KOLWI2VH-2 only by one amino acid at position 5(Q instead of V). Rat residues that are close to the CDRs, or known from prior experience to be important for interactions with the CDRs, were retained in both humanized sequences. A total of 5 rat residues were retained in the FR region of the humanized WI2 heavy chain sequence KOLWI2VH-1. The KOLWI2VH-2 sequence would have retained four rat aa residues.

The REI framework was chosen for grafting the light chain CDRs. Four rat residues were retained in the FR region of the designed light chain. The sequence of the designed light chain, REIWI2VK is shown in FIG. 2.

Gene Synthesis for Humanized WI2 VH and VK Domain

Using computer analysis, the nucleotide sequences encoding the humanized VH and VK domain of WI2 were assembled as follows.

hWI2 VH

The long oligo K (135-mer) was PCR-amplified using the flanking primers oligo 21 (45-mer) and oligo 22 (54-mer). The PCR product for oligo K encodes for the N-terminal half of the VH domain. Similarly, the long oligo L (133-mer) was PCR-amplified using the flanking primers oligo 23 (48-mer) and oligo 24 (45-mer). The PCR product for oligo L encodes for the C-terminal half of the VH domain. The sequences of the different oligos used for the PCR-synthesis of the humanized WI2 VH domain are summarized in FIG. 3.

The PCR product for oligo K was digested with PstI/AlwNI, whereas the PCR product for oligo L was digested with AlwNI/BstEII. The K and L fragments were gel-purified and ligated to the PstI/BstEII site of the staging, vector VHpBR. Minipreps were analyzed by restriction analysis as well as by sequencing reaction. MP33#4(1.6.95) was confirmed to have the correct sequence for the hWI2 VH, and was used for subsequent cloning and subcloning. The BamHI/HindIII fragment containing the hWI2 VH domain was gel-purified from the DNA after restriction digestion, and was cloned into the corresponding sites of the heavy chain expression vector, pG1g. Leung et al. *Hybridoma* 13:469 (1994).

hWI2 VK

The long oligo M' (129-mer) was PCR-amplified using the flanking primers oligo 25 containing a PvuII site and oligo 26. The PCR product for oligo M' encodes for the N-terminal half of the VK domain. The long oligo N (127-mer) was PCR-amplified by the flanking primers oligo 27 (44-mer) and oligo 28 (39-mer). The PCR product for oligo N encodes for the C-terminal half of the VK domain. The sequences of the oligonucleotides used for the PCR-amplification of the humanized WI2 VK domain are summarized in FIG. 4.

The PCR product for oligo M' was digested with PstI and PvuII, whereas the PCR product for oligo N was digested with PstI/BglII. The M and N fragments were gel-purified and ligated to the PvuII/BclI site of the staging vector VKpBR. By analysis of miniprep DNA three clones were identified to be the likely positives for hWI2VKpBR. Hogness stocks for these three minipreps were prepared. The sequence was confirmed from both directions, crossing the PvuII and BglII/BclI junctions. Plasmid DNA was prepared. The BamHI/HindIII fragment containing the hWI2 VK domain was gel-purified from the DNA after restriction digestion, and was cloned into the corresponding sites of the light chain expression vector, pKh. Id. Plasmid DNA for both the heavy and light chain vectors expressing hWI2 were prepared and cotransfected into SP2/O myeloma cells by electroporation.

A total of eight antibody producing colonies were identified using ELISA assays. The three highest producers were maintained and cell aliquots were frozen for storage. The highest producer was expanded and upscaled for subsequent antibody purification and testing.

Examining the Immunoreactivity of hWI2 Heavy Chain in a Mix-and-Match Experiment The mix-and-match antibody containing the humanized heavy and chimeric light chains of WI2 was purified. Various concentrations of the mix-and-match antibody were used to compete with ELISA-plate coated CEA for binding to the peroxidase-conjugated MN-14 antibody. Chimeric Ab was produced and expressed and shown to have immunogenic reactivity comparable to that of the rat WI2. The immunoreactivity of the mix-and-match WI2 was compared to that of cWI2, which has been confirmed to be identical to that of rat WI2. The humanized heavy chain for WI2 maintained the original immunoreactivity of rat WI2.

WI2

The original sequences for humanized WI2 heavy and light chains were designed from sequence homology comparison without the aid of computer modeling (FIG. 2). In a competitive binding assay, the first version of humanized WI2 (hWI2) was shown to be slightly less effective in blocking the binding of peroxidase conjugated MN-14 to CEA, as compared to that of rWI2 and cWI2 (FIG. 5). In the mix-and-match experiment (rVK+hVH) described above, it was demonstrated that the design of the humanized heavy chain was good. Therefore, a redesign of the humanized VK sequence was undertaken in an attempt to restore the full immunoreactivity of hwI2. Studies on the crystal structure for REI protein suggested that the rat residues Arg (66) and Ser (69) might be interacting with the light chain CDRs. These two rat residues, arg and ser were reintroduced into the VK FR3 of hWI2 by site-directed mutagenesis. The newly designed light chain, REIWI2VKRS is shown in FIG. 2. Humanized WI2 containing these two mutations was designated as hWI2RS. All mutations and vector constructions were confirmed by sequencing as well as by extensive restriction analysis. Expression vectors for this new version of humanized light chain (hWl2RSpKh) were used for transfection experiments by electroporation.

For unknown reasons, it had been difficult to get antibody producing clones transfected with the hWl2RS expression vector. Clones 131A9 and 132F7 were identified as positive clones producing about 0.4 and 0.2 mg/liter of hWl2RS antibodies, respectively. One liter cultures of clone 131A9 and 132F7 were grown in roller bottles and the antibody was purified by a standard protein purification method. Approximately 0.4 and 0.2 mg of hWl2RS was obtained from clone 131A9 and 132F7, respectively. The immunoreactivities of 131A9 and 132F7 hWl2RS, as measured by their abilities to block MN-14 binding on CEA, were shown to be similar.

EXAMPLE 2

Comparing the Immunoreactivities of Different Versions of WI2

In one experiment, the immunoreactivities of hWI2 and hWI2RS, as measured by their abilities to block MN-14 binding on CEA, were compared to that of rWI2 and cWI2, respectively (FIG. 5). Both hWI2 and hWI2RS appeared to exhibit a slightly reduced immunoreactivities than that of rWI2 and cWI2. The introduction of the RS mutation into the FR3 region of hWI2 did not seem to improve immunoreactivity as predicted. Nevertheless, hWI2 was nearly as immunoreactive as rWI2 or cWI2.

Both hWI2 and hWI2RS exhibited very similar, if not identical, immunoreactivity. Since hWI2RS contains two extra rat residues in the light chain FR3 region, and would be potentially more immunogenic the first humanized version of WI2, hWI2, was chosen to be the antibody that was further scaled up for production.

EXAMPLE 3

Construction of an Amplifiable Expression Vector for hWI2

The VH and VK sequence for hWI2 were excised from the respective staging vectors and ligated to a single amplifiable vector, pdHL2. The pdHL2 vector contains sequences for the human CK, IgG1, and an amplifiable DHFR gene, each controlled by separate promoters. See Leung et al., *Tumor Targeting* 2:184 (#95) (1996) and Losman et al., *Tumor Targeting* 2:183 (#93) (1996). The resultant vector expressing the hWI2 was designated hWI2pdHL2. The plasmid DNA for hWI2pdHL2 was linearized and transfected by electroporation into SP2/0 cells. Selection was performed by the addition of 0.1 μM of methotrexate (MTX) into the culture media. Amplification was carried out in a stepwise fashion with increasing concentration of MTX (from 0.1 to 3 μM). hWI2 purified from amplified clones exhibited identical immunoreactivity as hWI2 obtained from previous non-amplifiable clones.

```
                       SEQUENCE LISTING (1) GENERAL INFORMATION:

(iii) NUMBER OF SEQUENCES: 45

(2) INFORMATION FOR SEQ ID NO: 1:

(i) SEQUENCE CHARACTERISTICS:
             (A) LENGTH: 5 amino acids
             (B) TYPE: amino acid
             (C) STRANDEDNESS: <Unknown>
             (D) TOPOLOGY: linear (ii) MOLECULE TYPE: peptide (xi) SEQUENCE DESCRIPTION: SEQ ID NO: 1:

Asn Tyr Trp Met Thr
1               5

(2) INFORMATION FOR SEQ ID NO: 2:

(i) SEQUENCE CHARACTERISTICS:
             (A) LENGTH: 16 amino acids
             (B) TYPE: amino acid
             (C) STRANDEDNESS: <Unknown>
             (D) TOPOLOGY: linear (ii) MOLECULE TYPE: peptide (xi) SEQUENCE DESCRIPTION: SEQ ID NO: 2:

Ser Ile Thr Ser Thr Gly Gly Thr Tyr His Ala Glu Ser Val Lys Gly
1               5                   10                  15

(2) INFORMATION FOR SEQ ID NO: 3:

(i) SEQUENCE CHARACTERISTICS:
             (A) LENGTH: 13 amino acids
             (B) TYPE: amino acid
             (C) STRANDEDNESS: <Unknown>
             (D) TOPOLOGY: linear (ii) MOLECULE TYPE: peptide (xi) SEQUENCE DESCRIPTION: SEQ ID NO: 3:

Asp Asp Tyr Gly Gly Gln Ser Thr Tyr Val Met Asp Ala
1               5                   10
```

-continued

```
(2) INFORMATION FOR SEQ ID NO: 4:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 4:

Arg Ala Ser Gln Asp Ile Gly Asn Tyr Leu Arg
1               5                   10

(2) INFORMATION FOR SEQ ID NO: 5:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 5:

Gly Ala Thr Asn Leu Ala Ala
1               5

(2) INFORMATION FOR SEQ ID NO: 6:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 6:

Leu His His Ser Glu Tyr Pro Tyr Thr
1               5

(2) INFORMATION FOR SEQ ID NO: 7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 7:

GACGTATACC TGTGGTTTTC TG                                              22

(2) INFORMATION FOR SEQ ID NO: 8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 8:

AGGTSMARCT GCAGSAGTCW GG                                              22
```

```
(2) INFORMATION FOR SEQ ID NO: 9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 9:

TGAGGAGACG GTGACCGTGG TCCCTTGGCC CC                              32

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 10:

GGATGATGTC TTATGAACAA                                            20

(2) INFORMATION FOR SEQ ID NO: 11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 11:

CCAGTTCCGA GCTCGTGCTC ACCCAGTCTC CA                              32

(2) INFORMATION FOR SEQ ID NO: 12:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 12:

CCAGTTCCGA GCTCCAGATG ACCCAGTCTC CA                              32

(2) INFORMATION FOR SEQ ID NO: 13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 13:

CCAGATGTGA GCTCGTGATG ACCCAGACTC CA                              32
```

(2) INFORMATION FOR SEQ ID NO: 14:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 14:

```
CCAGATGTGA GCTCGTCATG ACCCAGTCTC CA                                  32
```

(2) INFORMATION FOR SEQ ID NO: 15:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 15:

```
CCAGTTCCGA GCTCGTGATG ACACAGTCTC CA                                  32
```

(2) INFORMATION FOR SEQ ID NO: 16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 16:

```
GTTAGATCTC CAGCTTGGTC CC                                             22
```

(2) INFORMATION FOR SEQ ID NO: 17:

(i) SEQUENCE CHARACTERISTICS:
        (A) LENGTH: 122 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 17:

```
Gln Val Gln Leu Val Glu Ser Gly Gly Gly Val Val Gln Pro Gly Arg
1               5                   10                  15

Ser Leu Arg Leu Ser Cys Ser Ser Gly Phe Ile Phe Ser Xaa Xaa
            20                  25                  30

Xaa Xaa Xaa Trp Val Arg Gln Ala Pro Gly Lys Gly Leu Glu Trp Val
        35                  40                  45

Ala Xaa Xaa Xaa Xaa Xaa Xaa Xaa Xaa Xaa Xaa Xaa Xaa Xaa Xaa Xaa
    50                  55                  60

Xaa Xaa Arg Phe Thr Ile Ser Arg Asp Asn Ser Lys Asn Thr Leu Phe
65                  70                  75                  80

Leu Gln Met Asp Ser Leu Arg Pro Glu Asp Thr Gly Val Tyr Phe Cys
                85                  90                  95
```

```
Ala Arg Xaa Xaa Xaa Xaa Xaa Xaa Xaa Xaa Xaa Xaa Xaa Xaa Trp
        100                 105                 110

Gly Gln Gly Thr Pro Val Thr Val Ser Ser
        115                 120

(2) INFORMATION FOR SEQ ID NO: 18:

(i) SEQUENCE CHARACTERISTICS:
        (A) LENGTH: 122 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 18:

Gln Val Gln Leu Gln Glu Ser Gly Gly Asp Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Thr Trp Ile Arg Gln Ala Pro Gly Glu Gly Leu Glu Trp Val
        35                  40                  45

Ala Ser Ile Thr Ser Thr Gly Gly Gly Thr Tyr His Ala Glu Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Pro Glu Asp Thr Ala Thr Tyr Tyr Cys
                85                  90                  95

Ser Arg Asp Asp Tyr Gly Gly Gln Ser Thr Tyr Val Met Asp Ala Trp
        100                 105                 110

Gly Gln Gly Ser Ser Val Thr Val Ser Ser
        115                 120

(2) INFORMATION FOR SEQ ID NO: 19:

(i) SEQUENCE CHARACTERISTICS:
        (A) LENGTH: 122 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 19:

Gln Val Gln Leu Gln Glu Ser Gly Gly Val Val Gln Pro Gly Arg
1               5                   10                  15

Ser Leu Arg Leu Ser Cys Ser Ser Ser Gly Phe Thr Phe Ser Asn Tyr
            20                  25                  30

Trp Met Thr Trp Ile Arg Gln Ala Pro Gly Lys Gly Leu Glu Trp Val
        35                  40                  45

Ala Ser Ile Thr Ser Thr Gly Gly Gly Thr Tyr His Ala Glu Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Pro Glu Asp Thr Gly Val Tyr Tyr Cys
                85                  90                  95

Ser Arg Asp Asp Tyr Gly Gly Gln Ser Thr Tyr Val Met Asp Ala Trp
        100                 105                 110

Gly Gln Gly Thr Pro Val Thr Val Ser Ser
        115                 120
```

(2) INFORMATION FOR SEQ ID NO: 20:

(i) SEQUENCE CHARACTERISTICS:
        (A) LENGTH: 122 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 20:

```
Gln Val Gln Leu Val Glu Ser Gly Gly Gly Val Val Gln Pro Gly Arg
1               5                   10                  15

Ser Leu Arg Leu Ser Cys Ser Ser Gly Phe Thr Phe Ser Asn Tyr
            20                  25                  30

Trp Met Thr Trp Ile Arg Gln Ala Pro Gly Lys Gly Leu Glu Trp Val
            35                  40                  45

Ala Ser Ile Thr Ser Thr Gly Gly Thr Tyr His Ala Glu Ser Val
50                  55                  60

Lys Gly Arg Phe Thr Ile Ser Arg Asp Asn Ser Lys Asn Thr Leu Phe
65                  70                  75                  80

Leu Gln Met Asp Ser Leu Arg Pro Glu Asp Thr Gly Val Tyr Tyr Cys
                85                  90                  95

Ser Arg Asp Asp Tyr Gly Gly Gln Ser Thr Tyr Val Met Asp Ala Trp
                100                 105                 110

Gly Gln Gly Thr Pro Val Thr Val Ser Ser
            115                 120
```

(2) INFORMATION FOR SEQ ID NO: 21:

(i) SEQUENCE CHARACTERISTICS:
        (A) LENGTH: 109 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 21:

```
Asp Ile Gln Met Thr Gln Ser Pro Ser Ser Leu Ser Ala Ser Val Gly
1               5                   10                  15

Asp Arg Val Thr Ile Thr Cys Xaa Xaa Xaa Xaa Xaa Xaa Xaa Xaa
            20                  25                  30

Xaa Xaa Trp Tyr Gln Gln Thr Pro Gly Lys Ala Pro Lys Leu Leu Ile
            35                  40                  45

Tyr Xaa Xaa Xaa Xaa Xaa Xaa Xaa Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Xaa Xaa Xaa Xaa Xaa Xaa Xaa
                85                  90                  95

Xaa Phe Gly Gln Gly Thr Lys Leu Gln Ile Thr Arg Thr
            100                 105
```

(2) INFORMATION FOR SEQ ID NO: 22:

(i) SEQUENCE CHARACTERISTICS:
        (A) LENGTH: 108 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 22:

```
Asp Ile Gln Leu Thr Gln Ser Pro Ala Ser Leu Pro Ala Ser Leu Gly
1               5                   10                  15

Asp Arg Val Thr Ile Thr Cys Arg Ala Ser Gln Asp Ile Gly Asn Tyr
                20                  25                  30

Leu Arg Trp Phe Gln Gln Lys Pro Gly Lys Pro Arg Leu Leu Ile
            35                  40                  45

Tyr Gly Ala Thr Asn Leu Ala Ala Gly Val Pro Ser Arg Phe Ser Gly
    50                  55                  60

Ser Arg Ser Gly Ser Asp Phe Ser Leu Thr Ile Asn Ser Leu Glu Ser
65                  70                  75                  80

Glu Asp Met Ala Ile Tyr Tyr Cys Leu His His Ser Glu Tyr Pro Tyr
                85                  90                  95

Thr Phe Gly Ile Gly Thr Lys Leu Glu Arg Lys Arg
                100                 105
```

(2) INFORMATION FOR SEQ ID NO: 23:

(i) SEQUENCE CHARACTERISTICS:
        (A) LENGTH: 108 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 23:

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
                20                  25                  30

Leu Arg Trp Phe Gln Gln Thr Pro Gly Lys Ala Pro Lys Leu Leu Ile
            35                  40                  45

Tyr Gly Ala Thr Asn Leu Ala Ala Gly Val Pro Ser Arg Phe Ser Gly
    50                  55                  60

Ser Arg Ser Gly Ser Asp Phe Thr Phe Thr Ile Ser Ser Leu Gln Pro
65                  70                  75                  80

Glu Asp Ile Ala Thr Tyr Tyr Cys Leu His His Ser Glu Tyr Pro Tyr
                85                  90                  95

Thr Phe Gly Ile Gly Thr Lys Leu Gln Ile Lys Arg
                100                 105
```

(2) INFORMATION FOR SEQ ID NO: 24:

(i) SEQUENCE CHARACTERISTICS:
        (A) LENGTH: 108 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 24:

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
                20                  25                  30
```

```
Leu Arg Trp Phe Gln Gln Thr Pro Gly Lys Ala Pro Lys Leu Leu Ile
        35                  40                  45

Tyr Gly Ala Thr Asn Leu Ala Ala Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu His His Ser Glu Tyr Pro Tyr
                85                  90                  95

Thr Phe Gly Ile Gly Thr Lys Leu Gln Ile Lys Arg
            100                 105

(2) INFORMATION FOR SEQ ID NO: 25:

(i) SEQUENCE CHARACTERISTICS:
        (A) LENGTH: 366 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..366

(xi) SEQUENCE DESCRIPTION: SEQ ID NO: 25:

CAG GTC CAA CTG CAG GAG TCA GGG GGA GGT GTA GTG CAG CCT GGA AGG      48
Gln Val Gln Leu Gln Glu Ser Gly Gly Gly Val Val Gln Pro Gly Arg
 1               5                  10                  15

TCT CTG AGA CTT TCC TGT AGC TCA TCT GGA TTC ACA TTC AGT AAT TAC      96
Ser Leu Arg Leu Ser Cys Ser Ser Ser Gly Phe Thr Phe Ser Asn Tyr
                20                  25                  30

TGG ATG ACT TGG ATA CGC CAG GCT CCA GGG AAG GGT CTT GAA TGG GTT     144
Trp Met Thr Trp Ile Arg Gln Ala Pro Gly Lys Gly Leu Glu Trp Val
            35                  40                  45

GCG TCC ATT ACT AGT ACT GGT GGT GGT ACC TAC CAT GCA GAG TCT GTG     192
Ala Ser Ile Thr Ser Thr Gly Gly Gly Thr Tyr His Ala Glu Ser Val
        50                  55                  60

AAG GGC CGA TTC ACT ATC TCC AGA GAT AAT TCA AAA AAC ACC CTG TTC     240
Lys Gly Arg Phe Thr Ile Ser Arg Asp Asn Ser Lys Asn Thr Leu Phe
65                  70                  75                  80

CTG CAA ATG GAC AGT CTG AGG CCT GAG GAC ACG GGC GTT TAT TAC TGT     288
Leu Gln Met Asp Ser Leu Arg Pro Glu Asp Thr Gly Val Tyr Tyr Cys
                85                  90                  95

TCA AGA GAT GAC TAC GGA GGA CAG AGC ACC TAT GTT ATG GAT GCC TGG     336
Ser Arg Asp Asp Tyr Gly Gly Gln Ser Thr Tyr Val Met Asp Ala Trp
            100                 105                 110

GGT CAG GGA ACT CCG GTC ACC GTC TCC TCC                             366
Gly Gln Gly Thr Pro Val Thr Val Ser Ser
        115                 120

(2) INFORMATION FOR SEQ ID NO: 26:

(i) SEQUENCE CHARACTERISTICS:
        (A) LENGTH: 122 amino acids
        (B) TYPE: amino acid
        (D) TOPOLOGY: linear (ii) MOLECULE TYPE: protein (xi) SEQUENCE DESCRIPTION: SEQ ID NO: 26:

Gln Val Gln Leu Gln Glu Ser Gly Gly Gly Val Val Gln Pro Gly Arg
 1               5                  10                  15
```

```
Ser Leu Arg Leu Ser Cys Ser Ser Gly Phe Thr Phe Ser Asn Tyr
         20                  25                  30

Trp Met Thr Trp Ile Arg Gln Ala Pro Gly Lys Gly Leu Glu Trp Val
             35                  40                  45

Ala Ser Ile Thr Ser Thr Gly Gly Thr Tyr His Ala Glu Ser Val
 50                  55                  60

Lys Gly Arg Phe Thr Ile Ser Arg Asp Asn Ser Lys Asn Thr Leu Phe
 65                  70                  75                  80

Leu Gln Met Asp Ser Leu Arg Pro Glu Asp Thr Gly Val Tyr Tyr Cys
                 85                  90                  95

Ser Arg Asp Asp Tyr Gly Gly Gln Ser Thr Tyr Val Met Asp Ala Trp
                100                 105                 110

Gly Gln Gly Thr Pro Val Thr Val Ser Ser
            115                 120
```

(2) INFORMATION FOR SEQ ID NO: 27:

(i) SEQUENCE CHARACTERISTICS:
        (A) LENGTH: 325 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..324

(xi) SEQUENCE DESCRIPTION: SEQ ID NO: 27:

```
GAC ATT CAG ATG ACC CAG TCT CCA TCT TCC CTG TCT GCG TCT GTG GGA      48
Asp Ile Gln Met Thr Gln Ser Pro Ser Ser Leu Ser Ala Ser Val Gly
 1               5                  10                  15

GAC AGA GTC ACT ATT ACT TGC CGG GCA AGT CAA GAC ATT GGA AAT TAT      96
Asp Arg Val Thr Ile Thr Cys Arg Ala Ser Gln Asp Ile Gly Asn Tyr
             20                  25                  30

TTA AGA TGG TTC CAG CAG ACA CCG GGG AAA GCT CCG AAA CTT TTG ATT     144
Leu Arg Trp Phe Gln Gln Thr Pro Gly Lys Ala Pro Lys Leu Leu Ile
         35                  40                  45

TAT GGT GCA ACC AAC TTG GCT GCA GGG GTC CCA TCA CGG TTC AGT GGC     192
Tyr Gly Ala Thr Asn Leu Ala Ala Gly Val Pro Ser Arg Phe Ser Gly
 50                  55                  60

AGT GGG TCT GGG ACA GAT TTT ACT TTT ACC ATC TCA AGC CTT CAG CCT     240
Ser Gly Ser Gly Thr Asp Phe Thr Phe Thr Ile Ser Ser Leu Gln Pro
 65                  70                  75                  80

GAA GAT ATT GCT ACT TAT TAC TGT CTG CAC CAT TCT GAG TAT CCA TAC     288
Glu Asp Ile Ala Thr Tyr Tyr Cys Leu His His Ser Glu Tyr Pro Tyr
                 85                  90                  95

ACG TTT GGA ATT GGG ACC AAG TTG CAG ATC AAA CGT G                   325
Thr Phe Gly Ile Gly Thr Lys Leu Gln Ile Lys Arg
                100                 105
```

(2) INFORMATION FOR SEQ ID NO: 28:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 28:

| Asp | Ile | Gln | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Arg | Ala | Ser | Gln | Asp | Ile | Gly | Asn | Tyr |
|---|---|---|---|---|---|---|---|---|---|---|---|---|---|---|---|
| | | | 20 | | | | | 25 | | | | | 30 | | |

| Leu | Arg | Trp | Phe | Gln | Gln | Thr | Pro | Gly | Lys | Ala | Pro | Lys | Leu | Leu | Ile |
|---|---|---|---|---|---|---|---|---|---|---|---|---|---|---|---|
| | | | 35 | | | | | 40 | | | | | 45 | | |

| Tyr | Gly | Ala | Thr | Asn | Leu | Ala | Ala | Gly | Val | Pro | Ser | Arg | Phe | Ser | Gly |
|---|---|---|---|---|---|---|---|---|---|---|---|---|---|---|---|
| | 50 | | | | 55 | | | | | 60 | | | | | |

| Ser | Gly | Ser | Gly | Thr | Asp | Phe | Thr | Phe | Thr | Ile | Ser | Ser | Leu | Gln | Pro |
|---|---|---|---|---|---|---|---|---|---|---|---|---|---|---|---|
| 65 | | | | | 70 | | | | | 75 | | | | | 80 |

| Glu | Asp | Ile | Ala | Thr | Tyr | Tyr | Cys | Leu | His | His | Ser | Glu | Tyr | Pro | Tyr |
|---|---|---|---|---|---|---|---|---|---|---|---|---|---|---|---|
| | | | | 85 | | | | | 90 | | | | | 95 | |

| Thr | Phe | Gly | Ile | Gly | Thr | Lys | Leu | Gln | Ile | Lys | Arg |
|---|---|---|---|---|---|---|---|---|---|---|---|
| | | | 100 | | | | | 105 | | | |

(2) INFORMATION FOR SEQ ID NO: 29:

(i) SEQUENCE CHARACTERISTICS:
        (A) LENGTH: 324 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..324

(xi) SEQUENCE DESCRIPTION: SEQ ID NO: 29:

```
GAC ATT CAG CTG ACC CAG TCT CCA GCT TCC CTG CCT GCG TCT CTG GGA      48
Asp Ile Gln Leu Thr Gln Ser Pro Ala Ser Leu Pro Ala Ser Leu Gly
 1               5                  10                  15

GAC AGA GTC ACT ATT ACT TGC CGG GCA AGT CAA GAC ATT GGA AAT TAT      96
Asp Arg Val Thr Ile Thr Cys Arg Ala Ser Gln Asp Ile Gly Asn Tyr
                20                  25                  30

TTA AGA TGG TTC CAG CAG AAA CCG GGG AAA TCT CCG AGG CTT TTG ATT     144
Leu Arg Trp Phe Gln Gln Lys Pro Gly Lys Ser Pro Arg Leu Leu Ile
            35                  40                  45

TAT GGT GCA ACC AAC TTG GCA GCT GGG GTC CCA TCA CGG TTC AGT CGC     192
Tyr Gly Ala Thr Asn Leu Ala Ala Gly Val Pro Ser Arg Phe Ser Arg
     50                  55                  60

AGT AGG TCT GGG TCA GAT TTT TCT CTG ACC ATC AAC AGC CTG GAG TCT     240
Ser Arg Ser Gly Ser Asp Phe Ser Leu Thr Ile Asn Ser Leu Glu Ser
 65                  70                  75                  80

GAA GAT ATG GCT ATT TAT TAC TGT CTG CAC CAT TCT GAG TAT CCA TAC     288
Glu Asp Met Ala Ile Tyr Tyr Cys Leu His His Ser Glu Tyr Pro Tyr
                85                  90                  95

ACG TTT GGA ATT GGG ACC AAG CTG GAA CGG AAA CGG                     324
Thr Phe Gly Ile Gly Thr Lys Leu Glu Arg Lys Arg
                100                 105
```

(2) INFORMATION FOR SEQ ID NO: 30:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 30:

```
Asp Ile Gln Leu Thr Gln Ser Pro Ala Ser Leu Pro Ala Ser Leu Gly
 1               5                  10                  15

Asp Arg Val Thr Ile Thr Cys Arg Ala Ser Gln Asp Ile Gly Asn Tyr
                20                  25                  30

Leu Arg Trp Phe Gln Gln Lys Pro Gly Lys Ser Pro Arg Leu Leu Ile
            35                  40                  45

Tyr Gly Ala Thr Asn Leu Ala Ala Gly Val Pro Ser Arg Phe Ser Arg
        50                  55                  60

Ser Arg Ser Gly Ser Asp Phe Ser Leu Thr Ile Asn Ser Leu Glu Ser
65                  70                  75                  80

Glu Asp Met Ala Ile Tyr Tyr Cys Leu His Ser Glu Tyr Pro Tyr
                85                  90                  95

Thr Phe Gly Ile Gly Thr Lys Leu Glu Arg Lys Arg
                100                 105
```

(2) INFORMATION FOR SEQ ID NO: 31:

(i) SEQUENCE CHARACTERISTICS:
        (A) LENGTH: 366 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..366

(xi) SEQUENCE DESCRIPTION: SEQ ID NO: 31:

```
CAG GTC CAA CTG CAG GAG TCA GGG GGA GAT CTA GTG CAG CCT GGA AGG      48
Gln Val Gln Leu Gln Glu Ser Gly Gly Asp Leu Val Gln Pro Gly Arg
 1               5                  10                  15

TCT CTG AAA CTT TCC TGT GTA GCC TCT GGA TTC ACA TTC AGT AAT TAC      96
Ser Leu Lys Leu Ser Cys Val Ala Ser Gly Phe Thr Phe Ser Asn Tyr
                20                  25                  30

TGG ATG ACT TGG ATC CGC CAG GCT CCA GGG GAG GGT CTT GAA TGG GTT     144
Trp Met Thr Trp Ile Arg Gln Ala Pro Gly Glu Gly Leu Glu Trp Val
            35                  40                  45

GCG TCC ATT ACT AGT ACT GGT GGT GGG ACT TAC CAT GCA GAG TCT GTG     192
Ala Ser Ile Thr Ser Thr Gly Gly Gly Thr Tyr His Ala Glu Ser Val
        50                  55                  60

AAG GGC CGA TTC ACT ATC TCC AGA GAT AAT TCA AAA AGC ACC CTG TAC     240
Lys Gly Arg Phe Thr Ile Ser Arg Asp Asn Ser Lys Ser Thr Leu Tyr
65                  70                  75                  80

CTG CAA ATG AAC AGT CTG AGG CCT GAG GAC ACG GCC ACT TAT TAC TGT     288
Leu Gln Met Asn Ser Leu Arg Pro Glu Asp Thr Ala Thr Tyr Tyr Cys
                85                  90                  95

TCA AGA GAT GAC TAC GGA GGA CAG AGC ACC TAT GTT ATG GAT GCC TGG     336
Ser Arg Asp Asp Tyr Gly Gly Gln Ser Thr Tyr Val Met Asp Ala Trp
                100                 105                 110

GGT CAG GGA TCT TCG GTC ACC GTC TCC TCA                             366
Gly Gln Gly Ser Ser Val Thr Val Ser Ser
            115                 120
```

(2) INFORMATION FOR SEQ ID NO: 32:

(i) SEQUENCE CHARACTERISTICS:
        (A) LENGTH: 122 amino acids
        (B) TYPE: amino acid
        (D) TOPOLOGY: linear (ii) MOLECULE TYPE: protein (xi) SEQUENCE DESCRIPTION: SEQ ID NO: 32:

Gln Val Gln Leu Gln Glu Ser Gly Gly Asp Leu Val Gln Pro Gly Arg
 1               5                  10                  15

Ser Leu Lys Leu Ser Cys Val Ala Ser Gly Phe Thr Phe Ser Asn Tyr
            20                  25                  30

Trp Met Thr Trp Ile Arg Gln Ala Pro Gly Glu Gly Leu Glu Trp Val
        35                  40                  45

Ala Ser Ile Thr Ser Thr Gly Gly Thr Tyr His Ala Glu Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Pro Glu Asp Thr Ala Thr Tyr Tyr Cys
                85                  90                  95

Ser Arg Asp Asp Tyr Gly Gly Gln Ser Thr Tyr Val Met Asp Ala Trp
            100                 105                 110

Gly Gln Gly Ser Ser Val Thr Val Ser Ser
        115                 120

(2) INFORMATION FOR SEQ ID NO: 33:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo"

(xi) SEQUENCE DESCRIPTION: SEQ ID NO: 33:

CAGGTCCAAC TGCAGGAGTC AGGGGGAGGT GTAGTGCAGC CTGGAA                46

(2) INFORMATION FOR SEQ ID NO: 34:

(i) SEQUENCE CHARACTERISTICS:
        (A) LENGTH: 130 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo"

(xi) SEQUENCE DESCRIPTION: SEQ ID NO: 34:

AGTAATGGAC GCAACCCATT CAAGACCCTT CCCTGGAGCC TGGCGTATCC AAGTCATCCA    60

GTAATTACTG AATGTGAATC CAGATGAGCT ACAGGAAAGT CTCAGAGACC TTCCAGGCTG   120

CACTACACCT                                                          130

(2) INFORMATION FOR SEQ ID NO: 35:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo"

(xi) SEQUENCE DESCRIPTION: SEQ ID NO: 35:

ATGCAGAGTC TGTGAAGGGC CGATTCACTA TCTCCAGAGA TAATTCAA                48

(2) INFORMATION FOR SEQ ID NO: 36:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo"

(xi) SEQUENCE DESCRIPTION: SEQ ID NO: 36:

```
TTCACAGACT CTGCATGGTA GGTACCACCA CCAGTACTAG TAATGGACGC AACC         54
```

(2) INFORMATION FOR SEQ ID NO: 37:

(i) SEQUENCE CHARACTERISTICS:
        (A) LENGTH: 133 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo"

(xi) SEQUENCE DESCRIPTION: SEQ ID NO: 37:

```
ACCCCAGGCA TCCATAACAT AGGTGCTCTG TCCTCCGTAG TCATCTCTTG AACAGTAATA   60

AACGCCCGTG TCCTCAGGCC TCAGACTGTC CATTTGCAGG AACAGGGTGT TTTTTGAATT  120

ATCTCTGGAG ATA                                                    133
```

(2) INFORMATION FOR SEQ ID NO: 38:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo"

(xi) SEQUENCE DESCRIPTION: SEQ ID NO: 38:

```
GGAGGAGACG GTGACCGGAG TTCCCTGACC CCAGGCATCC ATAAC                   45
```

(2) INFORMATION FOR SEQ ID NO: 39:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo"

(xi) SEQUENCE DESCRIPTION: SEQ ID NO: 39:

```
GACATTCAGC TGACCCAGTC TCCATCTTCC CTGTCTGCGT CTGTGGGAGA              50
```

(2) INFORMATION FOR SEQ ID NO: 40:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo"

(xi) SEQUENCE DESCRIPTION: SEQ ID NO: 40:

ATGACCCAGT CTCCATCTTC CCTGTCTGCG TCTGTGGGAG A                          41

(2) INFORMATION FOR SEQ ID NO: 41:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo"

(xi) SEQUENCE DESCRIPTION: SEQ ID NO: 41:

AGTTGGTTGC ACCATAAATC AAAAGTTTCG GAGCTTTCCC CGGTGTCTGC TGGAACCATC     60

TTAAATAATT TCCAATGTCT TGACTTGCCC GGCAAGTAAT AGTGACTCTG TCTCCCACAG    120

ACGCAGACA                                                            129

(2) INFORMATION FOR SEQ ID NO: 42:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo"

(xi) SEQUENCE DESCRIPTION: SEQ ID NO: 42:

TGGCTGCAGG GGTCCCATCA CGGTTCAGTG GCAGTGGGTC TGGG                      44

(2) INFORMATION FOR SEQ ID NO: 43:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo"

(xi) SEQUENCE DESCRIPTION: SEQ ID NO: 43:

GGACCCCTGC AGCCAAGTTG GTTGCACCAT AAATCA                               36

(2) INFORMATION FOR SEQ ID NO: 44:

(i) SEQUENCE CHARACTERISTICS:
        (A) LENGTH: 128 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo"

(xi) SEQUENCE DESCRIPTION: SEQ ID NO: 44:

TTGGTCCCAA TTCCAAACGT GTATGGATAC TCAGAATGGT GCAGACAGTA ATAAGTAGCA     60

ATATCTTCAG GCTGAAGGCT TGAGATGGTA AAAGTAAAAT CTGTCCCAGA CCCACTGCCA    120

CTGAACCG                                                             128

-continued (2) INFORMATION FOR SEQ ID NO: 45:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo"

(xi) SEQUENCE DESCRIPTION: SEQ ID NO: 45:

CACGTTAGAT CTGCAACTTG GTCCCAATTC CAAACGTGT                      39

What is claimed is:

1. An isolated expression vector comprising a first nucleic acid sequence that encodes a heavy chain variable region sequence comprising the CDR-1 sequence NYWMT (SEQ ID NO:1), CDR-2 sequence SITSTGGGTYHAESVKG (SEQ ID NO:2), and CDR-3 sequence DDYGGQSTYVMDA (SEQ ID NO:3) and a second nucleic acid sequence that encodes a light chain variable region sequence comprising the CDR1 sequence RASQDIGNYLR (SEQ ID NO:4), CDR2 sequence GATNLAA (SEQ ID NO:5), and the CDR3 sequence LHHSEYPYT (SEQ ID NO:6).

2. An isolated expression vector according to claim 1 wherein said light and heavy chains are chimeric or are humanized.

3. A host cell comprising said expression vector according to claim 1.

4. An isolated first expression vector comprising a nucleic acid sequence that encodes a heavy chain variable region sequence comprising the CDR-1 sequence NYWMT (SEQ ID NO:1), CDR-2 sequence SITSTGGGTYHAESVKG (SEQ ID NO:2), and CDR-3 sequence DDYGGQSTYVMDA (SEQ ID NO:3) and an isolated second expression vector comprising a nucleic acid sequence that encodes a light chain variable region sequence comprising the CDR1 sequence RASQDIGNYLR (SEQ ID NO:4), CDR2 sequence GATNLAA (SEQ ID NO:5), and CDR3 sequence LHHSEYPYT (SEQ ID NO:6).

5. An isolated first and second expression vectors according to claim 4, wherein said nucleic acid sequences encode a chimeric or humanized light and heavy chain.

6. A host cell comprising said first and second expression vectors according to claim 4.

7. A nucleic acid encoding a chimeric anti-idiotype antibody or fragment thereof, wherein said antibody or fragment thereof specifically binds to the idiotype region of an anti-CEA monoclonal antibody and the chimeric anti-idiotyne antibody or fragment comprises the light chain variable region sequence DIQLTQSPASLPASLGDRVTITCRASQDIGNYLRWFQQKPGKSPRLLIYGATNLAAGVPSRFSGSRSGSDFSLTINSLESEDMAIYYCLHHSEYPYTFGIGTKLERKR (SEQ ID NO:22) and heavy chain variable region sequence QVQLQESGGDLVQPGRSLKLSCVASGFTFSNYWMTWIRQAPGEGLEWVASITSTGGGTYHAESVKGRFTISRDNSKSTLYLQMNSLRPEDTATYYCSRDDYGGQSTYVMDAWGQGSSVTVSS (SEQ ID NO: 18).

8. A nucleic acid encoding a humanized anti-idiotype antibody or fragment thereof, wherein said antibody or fragment thereof specifically binds the idiotype region of an anti-CEA monoclonal antibody and the humanized anti-idiotyne antibody or fragment comprises CDR-1 sequence NYWMT (SEQ ID NO:1), CDR-2 sequence SITSTGGGTYHAESVKG (SEQ ID NO:2), CDR-3 sequence DDYGGQSTYVMDA (SEQ ID NO:3), CDR1 sequence RASQDIGNYLR (SEQ ID NO:4), CDR2 sequence GATNLAA (SEQ ID NO:5), and CDR3 sequence LHHSEYPYT (SEQ ID NO:6) and humanized FR regions.

9. A nucleic acid encoding an anti-idiotype antibody or fragment thereof, wherein said antibody or fragment thereof specifically binds the idiotype region of an anti-CEA monoclonal antibody and the anti-idiotype antibody or fragment comprises CDR-1 sequence NYWMT (SEQ ID NO:1), CDR-2 sequence SITSTGGGTYHAESVKG (SEQ ID NO:2), CDR-3 sequence DDYGGQSTYVMDA (SEQ ID NO:3), CDR1 sequence RASQDIGNYLR (SEQ ID NO:4), CDR2 sequence GATNLAA (SEQ ID NO:5), and CDR3 sequence LHHSEYPYT (SEQ ID NO:6).

* * * * *